(12) United States Patent
Park et al.

(10) Patent No.: US 12,186,580 B2
(45) Date of Patent: Jan. 7, 2025

(54) PATCH-TYPE SKINCARE DEVICE (71) Applicant: AMOSENSE CO., LTD, Cheonan-si (KR)

(72) Inventors: Jin Pyo Park, Cheonan-si (KR); Jun Ho Park, Cheonan-si (KR); Jung Bin Im, Cheonan-si (KR)

(73) Assignee: AMOSENSE CO., LTD., Cheonan-si (KR)

( * ) Notice: Subject to any disclaimer, the term of this patent is extended or adjusted under 35 U.S.C. 154(b) by 612 days.

(21) Appl. No.: 17/423,533

(22) PCT Filed: Jan. 15, 2020

(86) PCT No.: PCT/KR2020/000713
§ 371 (c)(1),
(2) Date: Jul. 16, 2021

(87) PCT Pub. No.: WO2020/149627
PCT Pub. Date: Jul. 23, 2020

(65) Prior Publication Data
US 2022/0072332 A1 Mar. 10, 2022

(30) Foreign Application Priority Data
Jan. 17, 2019 (KR) .................. 10-2019-0006142

(51) Int. Cl.
A61N 5/00 (2006.01)
A61N 1/32 (2006.01)
A61N 5/06 (2006.01)

(52) U.S. Cl.
CPC ........... A61N 5/0616 (2013.01); A61N 1/325 (2013.01); A61N 1/328 (2013.01);
(Continued)

(58) Field of Classification Search
CPC ...... A61N 5/0616; A61N 1/325; A61N 1/328; A61N 2005/0626; A61N 2005/0643;
(Continued)

(56) References Cited

U.S. PATENT DOCUMENTS

| 6,096,066 A | * | 8/2000 | Chen ................. A61N 5/062 |
| | | | 607/91 |
| 10,384,075 B2 | | 8/2019 | Iguchi et al. |
| 2012/0155057 A1 | | 6/2012 | McNeill et al. |

(Continued)

FOREIGN PATENT DOCUMENTS

| CN | 102591157 A | 7/2012 |
| CN | 103238020 A | 8/2013 |

(Continued)

OTHER PUBLICATIONS

International Search Report issued in PCT/KR2020/000713 dated Apr. 29, 2020, 2 pages.

(Continued)

Primary Examiner — Scott M. Getzow
(74) Attorney, Agent, or Firm — ROTHWELL, FIGG, ERNST & MANBECK, P.C.

(57) ABSTRACT

A patch-type skincare device is provided. A patch-type skincare device according to an exemplary embodiment of the present invention comprises: a light source part comprising a flexible plate-shaped substrate member having a circuit pattern formed on at least one surface thereof, and at least one LED mounted on one surface of the substrate member; a pair of cover members disposed on both surfaces of the substrate member so as to prevent the light source part from being exposed to the outside; and a connection cable for supplying the light source part with power that is externally supplied.

7 Claims, 6 Drawing Sheets (52) U.S. Cl.
CPC ............... *A61N 2005/0626* (2013.01); *A61N 2005/0643* (2013.01); *A61N 2005/0652* (2013.01); *A61N 2005/0658* (2013.01)

(58) Field of Classification Search
CPC .... A61N 2005/0652; A61N 2005/0658; A61N 2005/0651; A61N 1/0428; A61N 1/30; A61N 2005/0668
See application file for complete search history.

(56) References Cited

U.S. PATENT DOCUMENTS

| | | |
|---|---|---|
| 2013/0226269 A1 | 8/2013 | Eckhouse et al. |
| 2013/0229111 A1 | 9/2013 | Nakamura |
| 2014/0135874 A1 | 5/2014 | Dean et al. |
| 2015/0335788 A1* | 11/2015 | Xia ..................... A61L 27/58 424/444 |
| 2016/0015962 A1* | 1/2016 | Shokoueinejad Maragheh .......... A61N 1/32 607/88 |
| 2016/0256706 A1* | 9/2016 | Harrison ............ A61N 1/36003 |
| 2018/0015298 A1* | 1/2018 | Iguchi ..................... A61N 5/06 |
| 2018/0099143 A1 | 4/2018 | Kim et al. |
| 2019/0022406 A1* | 1/2019 | Hill ..................... A61F 13/0206 |
| 2020/0121941 A1 | 4/2020 | Kwon et al. |
| 2020/0069190 A1 | 5/2020 | Ryu et al. |

FOREIGN PATENT DOCUMENTS

| | | |
|---|---|---|
| CN | 109069853 A | 12/2018 |
| JP | 2012-532643 A | 12/2012 |
| JP | 2014-508542 A | 4/2014 |
| JP | 2017-006348 A | 1/2017 |
| JP | 2017153810 A | 9/2017 |
| KR | 20090055891 A | 6/2009 |
| KR | 1020110100122 A | 9/2011 |
| KR | 10-1192034 B1 | 10/2012 |
| KR | 20130110365 A | 10/2013 |
| KR | 10-1616002 B1 | 5/2016 |
| KR | 101642248 B1 | 7/2016 |
| KR | 10-2017-0004302 A | 1/2017 |
| KR | 20170140620 A | 12/2017 |
| KR | 10-2018-0092473 A | 8/2018 |
| WO | 2006/132551 A1 | 12/2006 |
| WO | 2016/136519 A1 | 9/2016 |

OTHER PUBLICATIONS

Japanese Office Action dated Jan. 24, 2023 issued in 2021-541141, 8 pgs.

Office Action dated Dec. 16, 2023 issued in corresponding Chinese Patent Application No. 202080009296.7 and translation (13 pages).

* cited by examiner

FIG. 8

PATCH-TYPE SKINCARE DEVICE

CROSS REFERENCE TO RELATED APPLICATIONS

This application is a 35 U.S.C. 371 National Phase Entry Application from PCT/KR2020/000713, filed Jan. 15, 2020, and designating the U.S., which claims the benefit of Korean Patent Application No. 10-2019-0006142 filed on Jan. 17, 2019, the disclosures of which are incorporated herein in their entirety by reference.

TECHNICAL FIELD

The present disclosure relates to a patch-type skincare device, and more particularly, to a patch-type skincare device capable of, in a state of being attached to the user's skin, improving the skin using light.

BACKGROUND ART

In recent years, research and development on skincare devices as a way of skin care that use a light source of a specific wavelength band to promote cell activity without thermal damage to skin tissue has been actively carried out.

However, conventional skincare devices are inconvenient to use because skincare using the devices is performed in a state in which the user holds the device by hand.

DISCLOSURE

Technical Problem

The present disclosure is directed to providing a patch-type skincare device capable of performing skincare in a state of being attached to the user's skin.

The present disclosure is also directed to providing a patch-type skincare device having flexibility and being implemented with a very small thickness, thus being capable of reducing the possibility of the device being separated from the user's skin.

Technical Solution

One aspect of the present disclosure provides a patch-type skincare device including a light source unit including a plate-shaped substrate member which has flexibility and has a circuit pattern formed on at least one surface thereof and at least one light-emitting diode (LED) which is mounted on one surface of the substrate member, a pair of cover members disposed on both surfaces of the substrate member to prevent the light source unit from being exposed to the outside, and a connection cable configured to supply the light source unit with power supplied from the outside.

Also, the substrate member may be a nanofiber web, which has a three-dimensional network structure having micropores, or a flexible printed circuit board.

Also, the LED may irradiate light in a wavelength band of 620 to 630 nm.

Also, the pair of cover members may be made of a material having moisture resistance and elasticity. For example, the cover member may be made of a silicone material.

Here, among the pair of cover members, a cover member covering the LED may be transparent, and the other cover member may be translucent or opaque.

Also, the connection cable may include a connection port provided at one end portion so as to be connected to an external power supply device, and the external power supply device may be a portable electronic device or a supplementary battery.

Also, the connection cable may further include a control unit configured to control the overall operation of the light source unit. For example, the control unit may be a remote control box.

Also, the light source unit may further include at least one temperature sensor mounted on one surface of the substrate member.

Also, the patch-type skincare device may further include at least one current applying member configured to apply current to a user's skin, and the current applying member may be disposed on an outer surface of the cover member. In such a case, the current applying member may be provided on an outer surface of the cover member covering the LED among the pair of cover members.

For example, the current applying member may be a conductive pattern printed on the outer surface of the cover member or a conductive member attached to the outer surface of the cover member.

Advantageous Effects

According to the present disclosure, since flexibility is secured, a patch-type skincare device can also be easily attached to a curved attachment portion, and adhesion of the patch-type skincare device with the skin can be improved.

Also, according to the present disclosure, since skin care can be performed in a state in which the patch-type skincare device is attached to the user's skin, convenience in use can be improved.

Further, since the patch-type skincare device according to the present disclosure has flexibility and is implemented with a very small thickness, a state in which the patch-type skincare device is attached to the user's skin can be maintained even without using a separate adhesive material. Accordingly, since the use of adhesive material is unnecessary, problems such as skin trouble due to the adhesive material may be prevented.

MODES OF THE INVENTION

Hereinafter, embodiments of the present disclosure will be described in detail with reference to the accompanying drawings to allow those of ordinary skill in the art to which the present disclosure pertains to easily practice the present disclosure. The present disclosure may be implemented in various different forms and is not limited to the embodiments described herein. In order to clearly describe the present disclosure, parts unrelated to the description have been omitted from the drawings, and the same or similar elements will be denoted by the same reference numerals throughout the specification.

Patch-type skincare devices 100 and 100' according to an embodiment of the present disclosure may, in a state of being attached to the user's skin, irradiate the user's skin with light in a predetermined wavelength band, thereby obtaining effects of soothing skin, improving skin texture, soothing sensitive skin, improving facial contour, improving skin elasticity, restoring skin elasticity, tightening skin, improving skin radiance, etc.

Here, the patch-type skincare devices 100 and 100' may be attached to the user's skin without using a separate adhesive or a sticking agent and may maintain the attached state even on a curved attachment portion such as a face.

For example, the patch-type skincare devices 100 and 100' may be attached to the skin through a liquid or gel material such as a material contained in an ampoule or another cosmetic material that is applied to the user's skin.

Figure 1:
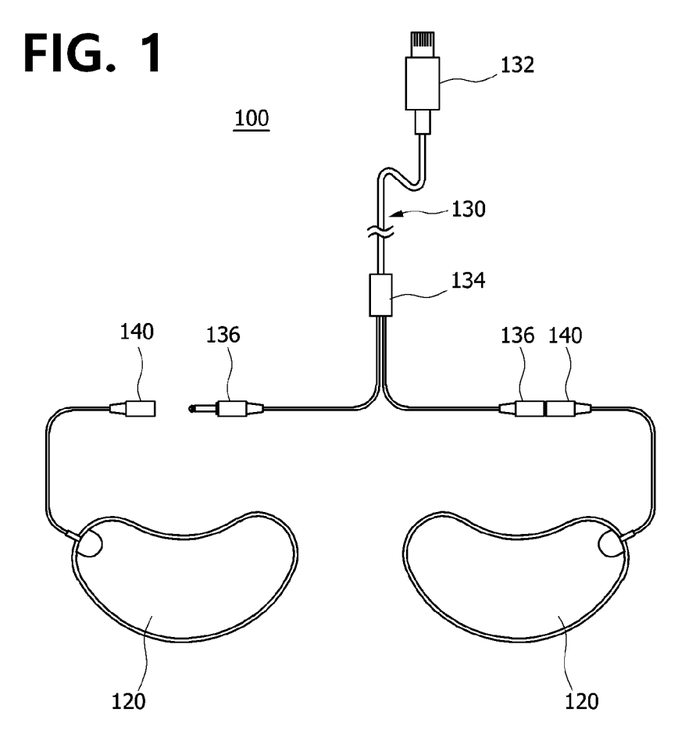
FIG. 1 is a view illustrating a patch-type skincare device according to an embodiment of the present disclosure.
Figure 6:
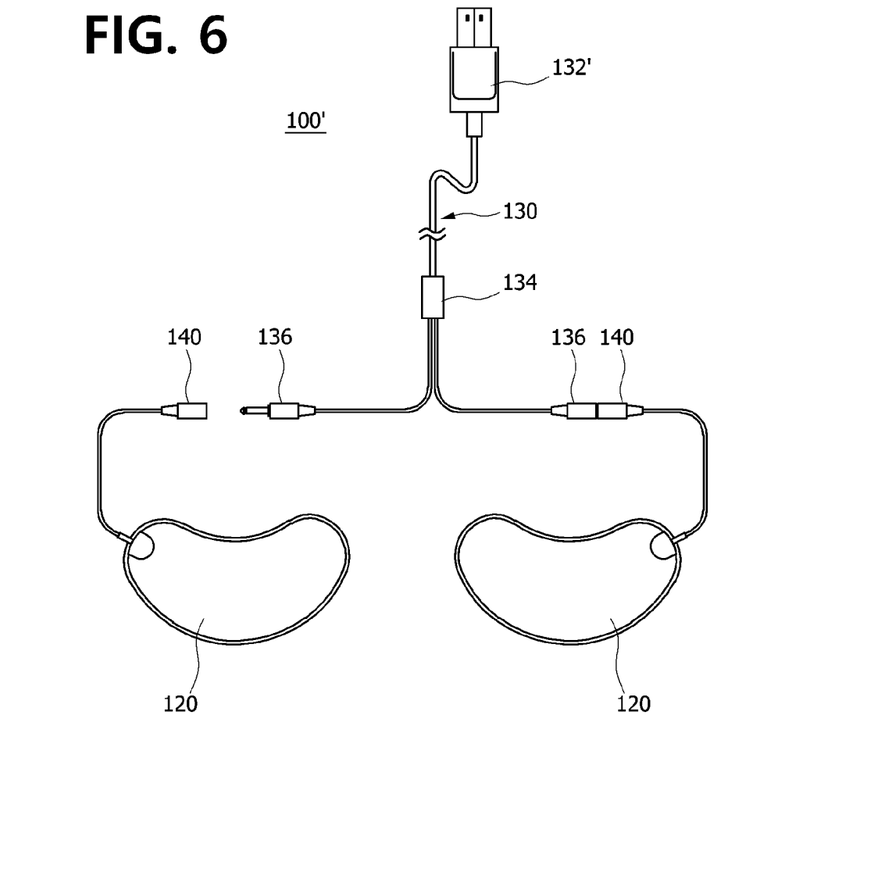
FIG. 6 is a view illustrating another form of cable in the patch-type skincare device according to an embodiment of the present disclosure.

To this end, as illustrated in FIGS. 1 and 6, the patch-type skincare devices 100 and 100' according to an embodiment of the present disclosure include a light source unit 110, a cover member 120, and connection cables 130 and 130'.

The light source unit 110 may irradiate light in a predetermined wavelength band using power supplied from the outside.

For example, the light source unit 110 may include a substrate member 111 and at least one light-emitting diode (LED) 112 mounted on one surface of the substrate member 111.

Here, the substrate member 111 may be a plate-shaped member having a circuit pattern 113 formed on at least one surface thereof, may have substantially the same shape as the cover member 120, and may be disposed inside the cover member 120.

Figure 4:
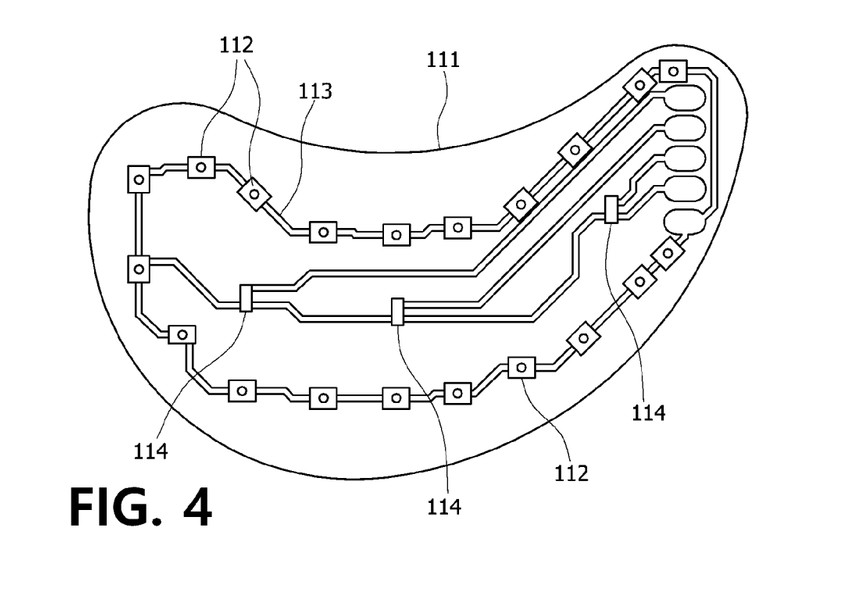
FIG. 4 is a view of the light source unit, which may be applied to the patch-type skincare device according to an embodiment of the present disclosure, from the top.

Accordingly, as illustrated in FIG. 4, a plurality of LEDs 112 may be arranged in a predetermined pattern on the substrate member 111, the plurality of LEDs 112 may be electrically connected to each other through the circuit pattern 113, and light irradiated from the plurality of LEDs 112 may be irradiated onto the user's skin over a wide area.

Here, the substrate member 111 may be made of a material having flexibility. Accordingly, even when one surface of the cover member 120 is attached to a curved portion such as the face, the substrate member 111 may be deformed corresponding to the curved portion, and thus the cover member 120 may maintain a state in close contact with the attachment portion.

For example, the substrate member 111 may be formed as a nanofiber web having micropores.

Figure 5:
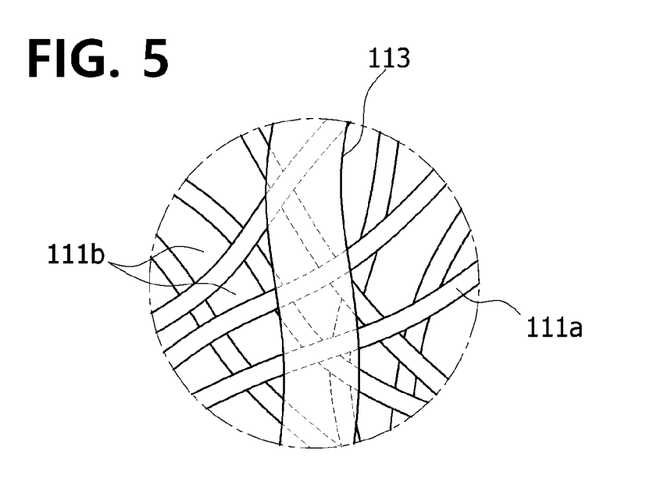
FIG. 5 is a view schematically illustrating a way in which a circuit pattern is formed on a substrate member in a case in which the substrate member is a nanofiber web in the patch-type skincare device according to an embodiment of the present disclosure.

As a specific example, as illustrated in FIG. 5, the substrate member 111 may be a nanofiber web in which nanofibers 111a including a synthetic polymer are accumulated in a three-dimensional network structure to have micropores 111b.

In such a case, the circuit pattern 113 may be formed as a predetermined pattern on one surface of the substrate member 111 through various known methods such as plating, etching, or printing using a conductive material, and the conductive material may fill in the micropores 111b.

For example, the circuit pattern 113 may be formed on the substrate member 111 through a printing method using a conductive paste, and the conductive paste may completely or partially fill the micropores 111b formed on the substrate member 111 as well as the one surface of the substrate member 111. Here, the conductive paste may be a Ag paste but is not limited thereto, and any other known conductive paste may be applied.

Accordingly, the substrate member 111 may serve as a printed circuit board. Since the substrate member 111 is formed as a nanofiber web as described above, the patch-type skincare devices 100 and 100' according to an embodiment of the present disclosure may have significantly higher bendability as compared to a polyimide film used as a general flexible printed circuit board and may have an excellent restoration characteristic that allows restoration to the original flat state even after being folded or wrinkled.

Also, since the conductive paste constituting the circuit pattern 113 fills the micropores 111b as well as the surface of the nanofiber web, the possibility of formation of cracks may be reduced even when the substrate member 111 is bent or wrinkled.

In addition, even when the substrate member 111 is bent or wrinkled and a crack is formed in a portion of the circuit pattern 113, at least some portions of the circuit pattern 113 may maintain a connected state through the paste that fills in the micropores 111b. Thus, the possibility of an occurrence of electrical short circuit may be significantly reduced.

Here, the micropores 111b may be formed to have an appropriate pore diameter size in consideration of a particle size of the paste. This is because, in a case in which the pore diameter size of the micropores is excessively small, infiltration or impregnation of the particles of the paste may not be facilitated.

As a specific example, the substrate member 111 may be a monolayer or multi-layer nanofiber web in which a spinning solution, in which a synthetic polymer and a solvent are mixed, is electrospun to be accumulated to have the micropores 111b. Here, the solvent may be water or alcohol or may also be an organic solvent other than water or alcohol.

Here, the synthetic polymer may be a fiber formation-type polymer that has elasticity and flexibility and is able to implement a nanofiber web through electrospinning. As a specific example, the synthetic polymer may have a form in which polyvinylidene fluoride (PVDF) is solely used or PVDF and polyurethane (PU) are mixed at a predetermined ratio but is not limited thereto, and any known material may be used so long as the material is a fiber formation-type polymer that is able to implement a nanofiber web through electrospinning and has elasticity and flexibility.

Since the substrate member 111 on which the circuit pattern 113 is formed on at least one surface thereof is implemented in the form of a nanofiber web having elasticity and flexibility, the patch-type skincare devices 100 and 100' according to an embodiment of the present disclosure may secure elasticity and flexibility.

Accordingly, even when attached to a curved portion of the skin such as the face, the patch-type skincare devices 100 and 100' according to an embodiment of the present disclosure may be naturally deformed corresponding to the curved portion. Thus, adhesion with the skin may be improved.

In addition, since the substrate member 111 on which the LED 112 is mounted is formed as a nanofiber web and may have a very small thickness, the patch-type skincare devices 100 and 100' may be implemented in a slim form. Accordingly, even when the patch-type skincare devices 100 and 100' according to an embodiment of the present disclosure are attached to the skin through a material such as a cosmetic material or a material contained in an ampoule, the possibility of the patch-type skincare devices 100 and 100' being separated from the user's skin may be reduced.

However, the substrate member 111 is not limited to the nanofiber web, and a known flexible printed circuit board (FPCB) on which a circuit pattern is formed on one surface thereof may also be used as the substrate member 111.

The LED 112 may generate light in a predetermined wavelength band to irradiate the user's skin with the light so that the user may obtain a beneficial effect according to the wavelength of the light.

The LED 112 may be provided as one or more LEDs 112. Preferably, as illustrated in FIG. 4, a plurality of LEDs 112 may be disposed to be spaced apart at predetermined intervals along the circuit pattern 113 formed on the substrate member 111. Accordingly, in the patch-type skincare devices 100 and 100' according to an embodiment of the present disclosure, the plurality of LEDs 112 may be disposed in a distributed form on the plate-shaped substrate member 111 and implemented in the form of a planar light source so that a wide area of the user's skin may be irradiated with light.

Here, the LED 112 may emit light in a single wavelength band. For example, the LED 112 may irradiate light in a wavelength band of 620 to 630 nm. However, the wavelength band of light emitted by the LED 112 is not limited thereto and may be appropriately changed to another wavelength band suitable for achieving a desired skin improvement effect.

In addition, the LED 112 may irradiate light in a single wavelength band but may also be provided to be able to irradiate light in different wavelength bands.

As a non-limiting example, in the LED 112, a plurality of light emitting elements configured to irradiate light in different wavelength bands may be integrally formed. That is, the LED 112 may be implemented in the form of a single chip by the plurality of light emitting elements, which are configured to irradiate light in different wavelength bands, being mounted on a single substrate.

Alternatively, as the LED 112, two or more LEDs 112 configured to irradiate light in different wavelength bands may be appropriately used.

The cover member 120 may be provided to surround the light source unit 110 and thus prevent the light source unit 110 from being exposed to the outside. Also, the cover member 120 may block a liquid material such as moisture applied to the user's skin from moving toward the light source unit 110.

To this end, the cover member 120 may be in the form of a plate-shaped sheet having a predetermined area to cover the light source unit 110.

The cover member 120 may be made of a material such as a polymer resin, i.e., PU, polyethylene terephthalate (PET), polypropylene (PP), polyethylene (PE), or PVDF, release paper, fabric, or leather, may be made of a silicone material, or may be in the form of a molding that is covered with a resin material made of an insulator.

That is, like the substrate member 111 having flexibility, the cover member 120 may be made of a material having flexibility and elasticity.

Also, the cover member 120 may be made of a material having moisture resistance in addition to flexibility and elasticity in order to block movement of moisture.

Figure 2:
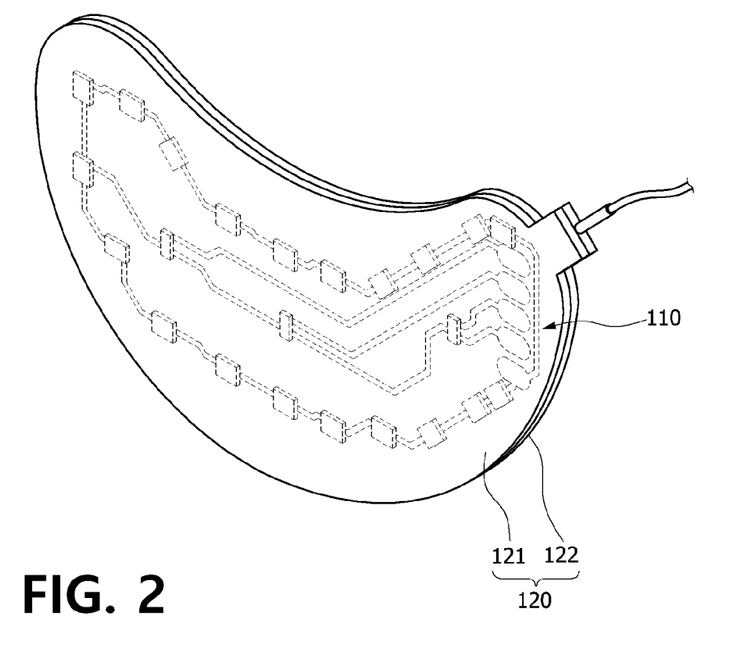
FIG. 2 is a view illustrating a light source unit and a cover member of FIG. 1.
Figure 3:
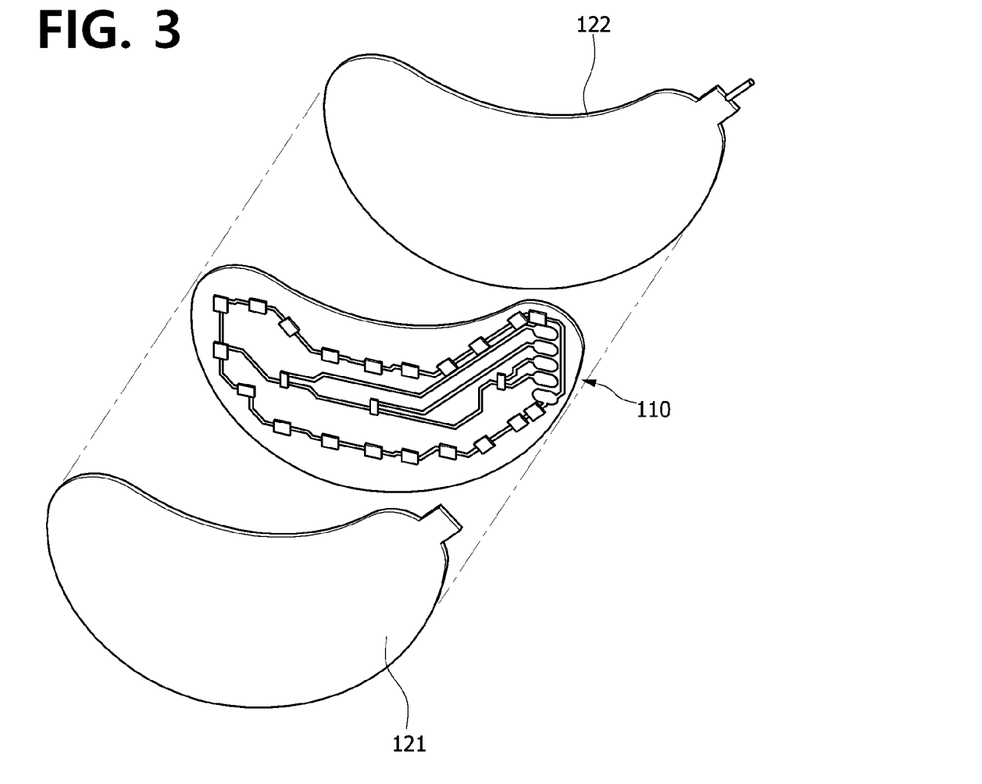
FIG. 3 is an exploded view of FIG. 2.

As a specific example, as illustrated in FIGS. 2 and 3, the cover member 120 may include a pair consisting of a first cover member 121 and a second cover member 122 disposed on both surfaces of the substrate member 111, and the first cover member 121 and the second cover member 122 may be attached through an adhesive layer or may be fixed to each other through heat fusion. Here, the adhesive layer may be a non-base material type of a liquid or gel or a base material type having an adhesive material applied to both surfaces thereof.

Also, the first cover member 121 may be a cover member that covers an upper portion of the LED 112, and the second cover member 122 may be a cover member that covers one surface of the substrate member 111 on which the LED 112 is not mounted. In such a case, the first cover member 121 may be a contact surface that comes in contact with the user's skin.

Here, the cover member 120 may be configured to limit a direction in which light generated from the LED 112 is irradiated. That is, any one of the first cover member 121 and the second cover member 122 may have transparency to allow light to pass therethrough, and the other one may have translucency or opacity to block passage of light.

For example, the first cover member 121 may have transparency, and the second cover member 122 may have translucency or opacity.

As a non-limiting example, the first cover member 121 may be made of a transparent silicone material, and the second cover member 122 may be made of a colored silicone material.

Accordingly, light generated from the LED 112 may pass through the first cover member 121 and be easily irradiated toward the user's skin, and irradiation of the light toward the outside may be prevented through the second cover member 122.

Meanwhile, as illustrated in FIGS. 1 and 6, the cover member 120 may have a shape including a portion in which a width is not uniform in one direction. For example, the cover member 120 may have one side formed in a shape that is concave inward and have a shape similar to the shape of an eyebrow. Also, the cover member 120 may have various other shapes such as a circular shape or an arc shape excluding a shape in which a width is uniform in the longitudinal direction, such as a rectangular shape or a square shape, or a polygonal shape excluding a rectangular shape.

However, the shape of the cover member 120 is not limited thereto, and the cover member 120 may also have a rectangular shape having a uniform width in the longitudinal direction.

The connection cable 130 may supply power supplied from the outside toward the light source unit 110.

To this end, the connection cable 130 may include connection ports 132 and 132' provided at one end portion so as to be connected to an external power supply device (not illustrated).

In addition, a connecting portion 136 electrically connected to the light source unit 110 may be provided at the other end portion side of the connection cable 130, and a portion to be connected 140 that is mutually connected to the connecting portion 136 may be provided to protrude outward from the cover member 120 in a state of being electrically connected to the light source unit 110.

Accordingly, the light source unit 110 may be operated using the power provided from the external power supply device through the connection cable 130.

Here, the external power supply device may be a portable electronic device such as a mobile phone or may be a supplementary battery. In addition, the connection ports 132 and 132' may be appropriately changed according to the shape of the external power supply device.

For example, as illustrated in FIG. 1, the connection port 132 may be a 5-pin, 8-pin, or C-type terminal part so as to be connected to a portable electronic device, and as illustrated in FIG. 6, the connection port 132' may be in the form of a universal serial bus (USB) so as to be connected to a known supplementary battery.

Here, the connection cable 130 may further include a control unit 134 configured to manipulate the operation of the light source unit 110. For example, the control unit 134 may be implemented as a remote controller-type control box, which is able to be manipulated by a user, and may be disposed at an intermediate portion of the connection cable 130. In addition, the control unit 134 may include a controller to control the overall operation of the light source unit 110. For example, the control unit 134 may control the on/off of the light source unit 110, selection or change of a light emitting mode of the light source unit, a function that allows automatic turn-off of the light source unit after a certain amount of time, and the like.

Meanwhile, the light source unit 110 may further include at least one temperature sensor 114 mounted on one surface of the substrate member 111. The temperature sensor 114 may measure the temperature generated when the LED 112 emits light and may provide the measured temperature information to the control unit 134. Accordingly, the control unit 134 may control the on/off operation of the light source unit 110 on the basis of the temperature information transmitted from the temperature sensor 114 and thus prevent the user from getting burned due to heat generated from the light source unit 110.

Here, an appropriate number of temperature sensors 114 may be mounted on one surface of the substrate member 111, and the temperature sensors 114 may be distributed to measure the temperature at various positions.

Meanwhile, the patch-type skincare devices 100 and 100' according to an embodiment of the present disclosure may include a known iontophoresis function.

That is, the patch-type skincare devices 100 and 100' according to an embodiment of the present disclosure may include a current applying member 150 configured to, when power is applied thereto, generate a potential difference in the user's skin and change an electrical environment of the skin to increase penetration of ionic drug through the skin.

When power is supplied to the current applying member 150 in a state in which the current applying member 150 is in contact with the user's skin, the current applying member 150 may apply DC current to the user's skin to move ions.

Accordingly, when, in a state in which the current applying member 150 is in contact with the user's skin to which a cosmetic material is applied, DC current is applied by the current applying member 150 to ionize the cosmetic material applied to the user's skin, it is possible to obtain an ion introduction effect that allows the cosmetic material to easily pass through the mucosa of the skin and penetrate through tissues in the skin.

Figure 7:
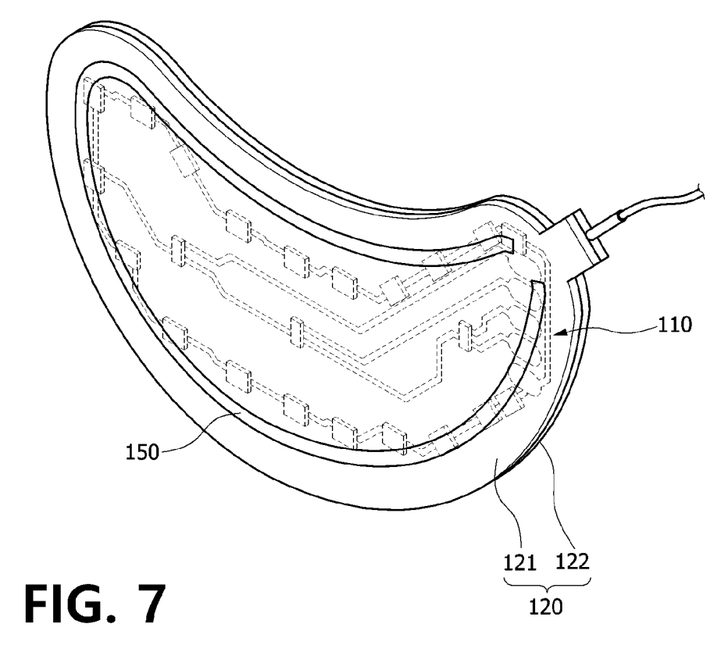
FIG. 7 is a view illustrating a case in which a current applying member is included in FIG. 2.
Figure 8:
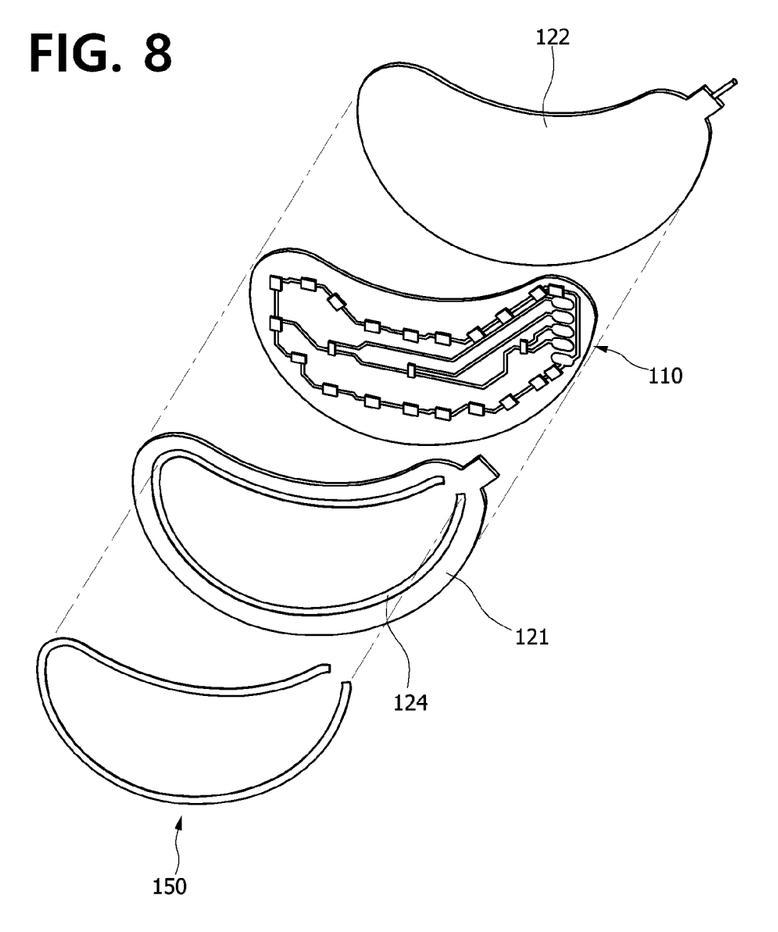
FIG. 8 is an exploded view of FIG. 7.

To this end, as illustrated in FIGS. 7 and 8, the current applying member 150 may be provided on one surface of the cover member 120, and the current applying member 150 may be provided on an outer surface of the first cover member 121 that comes in direct contact with the user's skin while covering the LED 112 among the pair of cover members 120.

Accordingly, when, in a state in which a cosmetic material is applied to a portion of the user's body to be treated, the user attaches the first cover member 121 to the portion through a cosmetic material, the current applying member 150 formed on the outer surface of the first cover member 121 may maintain a state of being in contact with the portion of the body.

Thus, the user may simultaneously obtain a skin improvement effect due to the LED of the light source unit 110 and use the iontophoresis function using the current applying member 150.

Here, as illustrated in FIG. 8, the current applying member 150 may be a conductive member attached to the outer surface of the first cover member 121, and the conductive member may be inserted into an accommodation groove 124 formed in the outer surface of the first cover member 121.

Alternatively, the current applying member 150 may also be a conductive pattern printed on the outer surface of the first cover member 121.

Although the current applying member 150 is illustrated in the drawings as being provided as a single member, the current applying member 150 is not limited thereto and may also be formed as two members separated from each other.

Exemplary embodiments of the present disclosure have been described above, but the spirit of the present disclosure is not limited by the embodiments proposed herein. Those of ordinary skill in the art who understand the spirit of the present disclosure may easily propose other embodiments by addition, modification, omission, or the like of elements within the same spirit, but such changes also belong to the scope of the spirit of the present disclosure.

The invention claimed is:

1. A patch-type skincare device comprising:
   a light source unit including a plate-shaped substrate member which has flexibility and has a circuit pattern on a first surface of the substrate member, a light-emitting diode (LED) on the first surface of the substrate member, and a temperature sensor on the first surface of the substrate member, which is configured to measure a temperature generated when the LED emits light;
   a pair of cover members disposed on the first surface and a second surface of the substrate member to prevent the light source unit from being exposed to an outside;
   a connection cable configured to supply the light source unit with power supplied from the outside and
   a current applying member configured to apply current to a user's skin,
   wherein the connection cable comprises a control unit configured to control operation of the light source unit,
   wherein the control unit controls an on/off operation of the light source unit based on temperature information transmitted from the temperature sensor,
   wherein the pair of cover members includes a first cover member which covers the LED and is transparent, and a second cover member which is translucent or opaque, and
   wherein the current applying member is disposed on an outer surface of the first cover member.

2. The patch-type skincare device of claim 1, wherein the substrate member is a nanofiber web that has a three-dimensional network structure having micropores.

3. The patch-type skincare device of claim 1, wherein the LED irradiates light in a wavelength band of 620 to 630 nm.

4. The patch-type skincare device of claim 1, wherein the substrate member is a flexible printed circuit board.

5. The patch-type skincare device of claim 1, wherein the pair of cover members are made of a material having moisture resistance and elasticity.

6. The patch-type skincare device of claim 1, wherein:
the connection cable includes a connection port provided at one end portion so as to be connected to an external power supply device; and
the external power supply device is a portable electronic device or a supplementary battery.

7. The patch-type skincare device of claim 1, wherein the current applying member is a conductive pattern printed on the outer surface of the first cover member or a conductive member covering the LED attached to the outer surface of the first cover member covering the LED.

\* \* \* \* \*